United States Patent
Ellman et al.

(10) Patent No.: US 6,562,032 B1
(45) Date of Patent: May 13, 2003

(54) ELECTROSURGICAL INSTRUMENT WITH VIBRATION

(76) Inventors: Alan G. Ellman, 1135 Railroad Ave., Hewlett, NY (US) 11557; Jon C. Garito, 1135 Railroad Ave., Hewlett, NY (US) 11557

( * ) Notice: Subject to any disclaimer, the term of this patent is extended or adjusted under 35 U.S.C. 154(b) by 91 days.

(21) Appl. No.: 09/817,382

(22) Filed: Mar. 26, 2001

(51) Int. Cl.[7] ................................................ A61B 18/00
(52) U.S. Cl. ............................ 606/41; 606/45; 606/49
(58) Field of Search ............................. 606/40–42, 45, 606/48–50; 601/1–3

(56) References Cited

U.S. PATENT DOCUMENTS

| | | | | |
|---|---|---|---|---|
| 4,886,060 A | * | 12/1989 | Wiksell | 606/39 |
| 4,931,047 A | * | 6/1990 | Broadwin et al. | 604/22 |
| 5,836,897 A | * | 11/1998 | Sakurai et al. | 606/40 |
| 5,948,009 A | * | 9/1999 | Tu | 607/96 |
| 6,050,993 A | * | 4/2000 | Tu et al. | 606/41 |
| 6,206,842 B1 | * | 3/2001 | Tu et al. | 606/128 |
| 6,251,110 B1 | * | 6/2001 | Wampler | 606/49 |

FOREIGN PATENT DOCUMENTS

| | | | |
|---|---|---|---|
| JP | 7-95985 | * | 4/1995 |
| JP | 8-168495 | * | 7/1996 |

* cited by examiner

*Primary Examiner*—John A. Jeffery

(57) ABSTRACT

A combination electrosurgical instrument and vibratory device provides simultaneous transmission of radiofrequency energy and vibratory ultrasonic energy via a simple efficient handpiece attachment enabling a surgeon to modulate all types of tissues with different degrees of effectiveness. The combination of the invention enhances the proven effectiveness of both radiofrequency and ultrasonic technology. In a preferred embodiment, a small unbalanced motor that vibrates when activated is used to cause an electrosurgical handpiece containing the electrosurgical electrode to vibrate as a whole and to transmit to the electrode ultrasonic energy. The invention is of especial value when applied to skin resurfacing, but will also be of value for tissue modulation, coagulation, hemostasis and other electrosurgical procedures.

13 Claims, 4 Drawing Sheets

US 6,562,032 B1

ELECTROSURGICAL INSTRUMENT WITH VIBRATION

This invention relates to an electrosurgical instrument useful for tissue modulation, skin resurfacing, coagulation, hemostasis and other electrosurgical procedures. It also relates to an attachment for a standard electrosurgical handpiece that will cause the electrosurgical electrode to vibrate when activated.

BACKGROUND OF THE INVENTION

Ultrasonic-ultrasound technology used in conjunction with a standard surgical scalpel is a known surgical procedure. It typically has the following disadvantages:

The surgical blades must be sharp, similar to scalpel blades.

The cutting speed and coagulation effect are inversely related. With ultrasound/ultrasonic technology, it is important to control or balance a number of factors for good surgical results, including (a) power (b) blade sharpness (c) tissue tension (d) grip force/pressure.

(a) Power-increasing power increases cutting speed but decreases coagulation; less power decreases cutting speed and increases coagulation. The ultrasonic vibration is typically 55,500 Hz and remains the same at all power levels.

(b) Blade Sharpness-Blades must be sharp to get cutting results.

(c) Tissue Tension-More coagulation is achieved with slower cutting when tissue tension is reduced. Faster cutting results in less coagulation by increasing tissue tension.

(d) Grip Force/Pressure—Gentle force or light pressure achieves more coagulation with slower cutting. A firmer grip force achieves less coagulation and faster cutting. The balance is often difficult for the surgeon to control. Dissection cutting uses force directed energy. Cavitational bubbles can result from pressure differentials at the ultrasonic blade tip.

The typical components of an ultrasonic scalpel are:

Generator—Microprocessor-controlled high frequency switching power supply that drives the acoustic system in the handpiece.

Handpiece—Contains a transducer that consists of a piezoelectric ceramic that expands and contracts to convert the electrical energy from the generator into mechanical vibration. The ultrasonic vibration is transmitted from the transducer through an extending rod to the attached scalpel blade. The blade extender is supported by silicone rings positioned at nodes to direct the flow of energy in a longitudinal direction and to prevent energy from being dissipated on the sheath.

While it is believed that others may have attempted to convert the ultrasonic scalpel to electrosurgery, to our knowledge, such attempts have not proven satisfactory, mainly because the use of the standard ceramic transducer imposed unreasonable demands of size and power in order to produce sufficient ultrasonic wave generation within the handpiece.

SUMMARY OF THE INVENTION

An object of the invention is an improved electrosurgical instrument for applying electrosurgical currents to the tissue of a patient in a more effective and controlled manner.

Another object of the invention is a procedure for more evenly distributing electrosurgical currents to the tissue of a patient being treated.

The essence of the invention is to vibrate the active electrosurgical electrode that modulates the patient's tissue. We have found that vibrating the electrode causes a more even distribution of the RF electrosurgical currents to the tissue site being treated. In addition, another advantage of the vibration is that it enhances the effectiveness of the radiofrequency energy because it allows minimal tissue contact and a superficial light touch. The normal reaction is for the surgeon to use pressure during surgical procedures that actually reduces the effect of the radiofrequency energy on the tissue. With RF electrosurgical currents, the lighter the touch or contact, the greater the effect of the radiofrequency energy on the water molecules of the tissue in contact. The enhancement of the vibration reduces the normal reaction of pressure and enhances the radio frequency performance by allowing a light touch to the tissue thereby creating maximum performance out of the radiofrequency device. Less tissue contact equals better performance.

In accordance with a preferred embodiment of the invention, simultaneous transmission of radiofrequency energy and vibratory ultrasonic energy via a simple efficient handpiece attachment enables a surgeon to modulate all types of tissues with different degrees of effectiveness. The combination of the invention enhances the proven effectiveness of both radiofrequency and ultrasonic technology.

The invention is of especial value when applied to skin resurfacing, but will also be of value for tissue modulation, coagulation, hemostasis and other electrosurgical procedures. In an electrosurgical skin planing procedure, it enables physicians to offer to patients a dermatologic treatment that is efficiently performed, easily learned and thus performed at a significantly reduced cost, with less tissue damage compared to procedures done heretofore, and, most important, with better control over the depth of skin treatment. Other disciplines that can use this technology include neurosurgery, laparoscopy, gynecology, urology, and head and neck surgery.

Vibration of the electrode can be achieved by vibrating the entire handpiece that holds the electrode or by transferring the effect of the vibration to the active part of the electrode. It will prove of benefit with various known electrode shapes and sizes, including the electrode described in U.S. Pat. No. 5,746,746.

In accordance with another preferred embodiment of the invention, we have found an improved surgical effect by adding to a standard radiofrequency (RF) electrosurgical handpiece a vibrator device capable of vibrating at a speed of the order of 8,000–12,000 revolutions per minute (8K–12K rpm).

In accordance with another preferred embodiment of the invention, experiments have demonstrated that when a vibrational effect at approximately 10K rpm is combined radiofrequency energy such as produced with the ellman Surgitron Dual Frequency electrosurgical unit by attaching a vibrator device onto the RF handpiece, improved performance is achieved when the vibrational radiofrequency is realized and simultaneously applied by applying RF energy and switching on the vibrator to vibrate the electrosurgical electrode mounted in the standard handpiece or any electrosurgical device. Among other things, it is highly effective in rapidly moving through all tissue thickness for a complete cutting effect with little to no adjacent tissue charring. The effect of the vibration offers the advantage of even distribution of the RF energy to the skin surface. This even distributon of radiofreqency has the advantage that it cannot be ordinarily obtained by the use merely of manual light touch of the surgeon. Since the RF energy effect is increased by the lighter touch or minimal contact with the skin surface or tissue, the combination of the ultrasonic effect added to the RF electrode produces maximum effect of the RF energy.

Further, each waveform mode of the RF energy is greatly enhanced by the simultaneous application of the vibratory activity. Cutting alone with the RF current and vibration becomes much faster, and movement through the tissue meets much less resistance. In the cut and coagulation mode, a fast movement through tissue is realized while simultaneously creating a more aggressive coagulation of blood vessels. The hemostatic effect while quickly and smoothly cutting is quite controlled while reducing the margin of burned tissue edges. In the coagulation mode, the simultaneously combing of vibration with RF energy quickly allows a rapid hemostasis and control of bleeding vessels.

Among the procedures for which the invention is especially suitable, but to which it is not limited, are dermal browlift, removing vascular lesions, hair removal, skin resurfacing, and tissue vaporization of skin lesions.

The electrosurgical procedure has the important advantage of being able to remove tissue with minimum surgeon pressure while at the same time coagulating the cut tissue causing minimum bleeding. It is preferred that the electrosurgical currents used be above 2 MHz, and preferably about 4 MHz. At these high frequencies, commonly referred to as radiosurgery, cutting is accomplished by volatilizing intracellular fluids at the point of the transmitting electrode contact which is primarily responsible for only small lateral heat spread and thus less damage to neighboring cell layers.

Although it is preferred that the radiosurgery device be above 2 MHz, and preferably about 4 MHz, it will be realized that the effect of the vibration will enhance even lower frequency electrosurgery instruments.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF THE PREFERRED EMBODIMENTS

Figure 1:
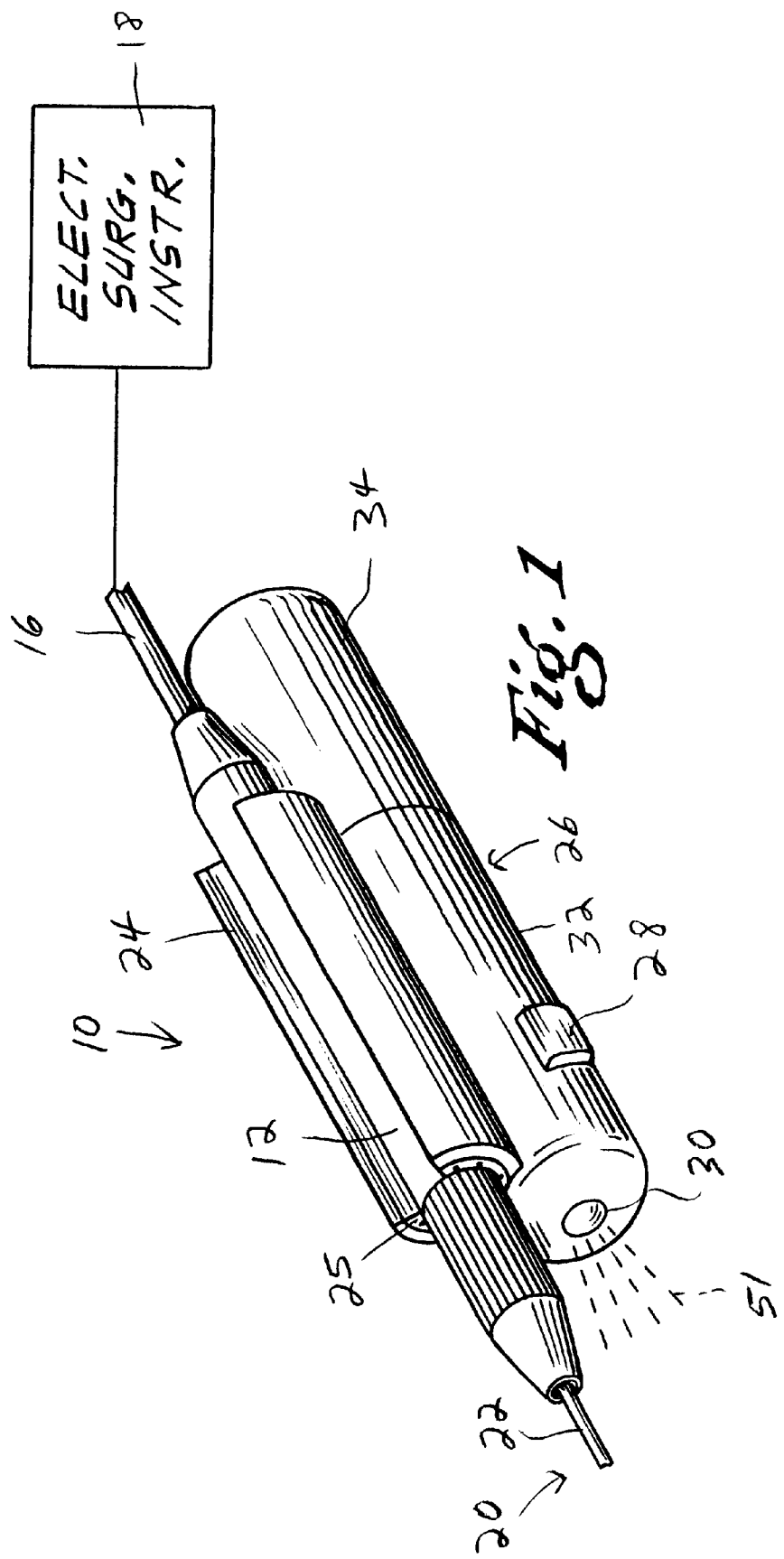
FIG. 1 is a perspective view of one form of electrosurgical instrument in accordance with the invention, shown connected to electrosurgical apparatus.

FIG. 1 illustrates a preferred form of the novel electrosurgical instrument 10 of the invention. It comprises an elongated conventional handpiece 12 of electrically-insulating material having a central electrically-conductive tube or conductor (not shown) extending throughout its length and connected at its end to a cable 16 which is connected in the conventional manner to conventional electrosurgical apparatus 18. As examples only, the electrosurgical apparatus can be model AAOP Surgitron FFPF or Dual Frequency electrosurgical unit available from Ellman International, Inc. of Hewlett, N.Y. The Ellman equipment is preferred due to its high operating frequency, typically above 2 MHz, preferably above 3 MHz; however it will also be realized that the effect of the vibration will enhance any RF electrocautery device. This particular apparatus provides electrosurgical currents at 3.8 MHz.

At the opposite end of the handpiece 12 is mounted the electrosurgical electrode 20 which comprises an electrically-conductive straight axial brass rod 22 running lengthwise through it and mounted at its end nearest the handpiece 12 in the handpiece collet and thus electrically connected to the electrically-conductive cable 16. The distal or working end of the electrode (not shown) can be any one of the shapes and sizes well known in the art, examples being shown in Ellman catalogs, and comprises an electrically-conductive working surface electrically connected to the brass rod 22 and from which are generated the electrosurgical currents to the operative site when the electrosurgical unit 18 is activated. Also connected to the electrosurgical apparatus 18 is the usual indifferent plate (not shown) which during use is in contact with a patient's body. When the electrosurgical apparatus 18 is energized, high frequency electrosurgical currents are generated which are coupled by way of the cable 16 and electrically-conductive rod 22 to the notshown working end. The handpiece 12, which preferably is a standard handpiece, is removably mounted in a semi-cylindrical holder, for example, of plastic, lined on its interior with a friction-aiding material 25 such as rubber. The handpiece holder 24 is mounted on a cylindrical housing 26 having on its side a pushbutton cover 28 and at its front an optically-transparent region 30 which may be an opening, a lens or a plate. The physician, in the usual way, holds the assembly 10 while applying the active working end of the electrode to the desired area of the patient to be treated and then presses the pushbutton 28 while activating the electrosurgical unit 18.

Figure 2:
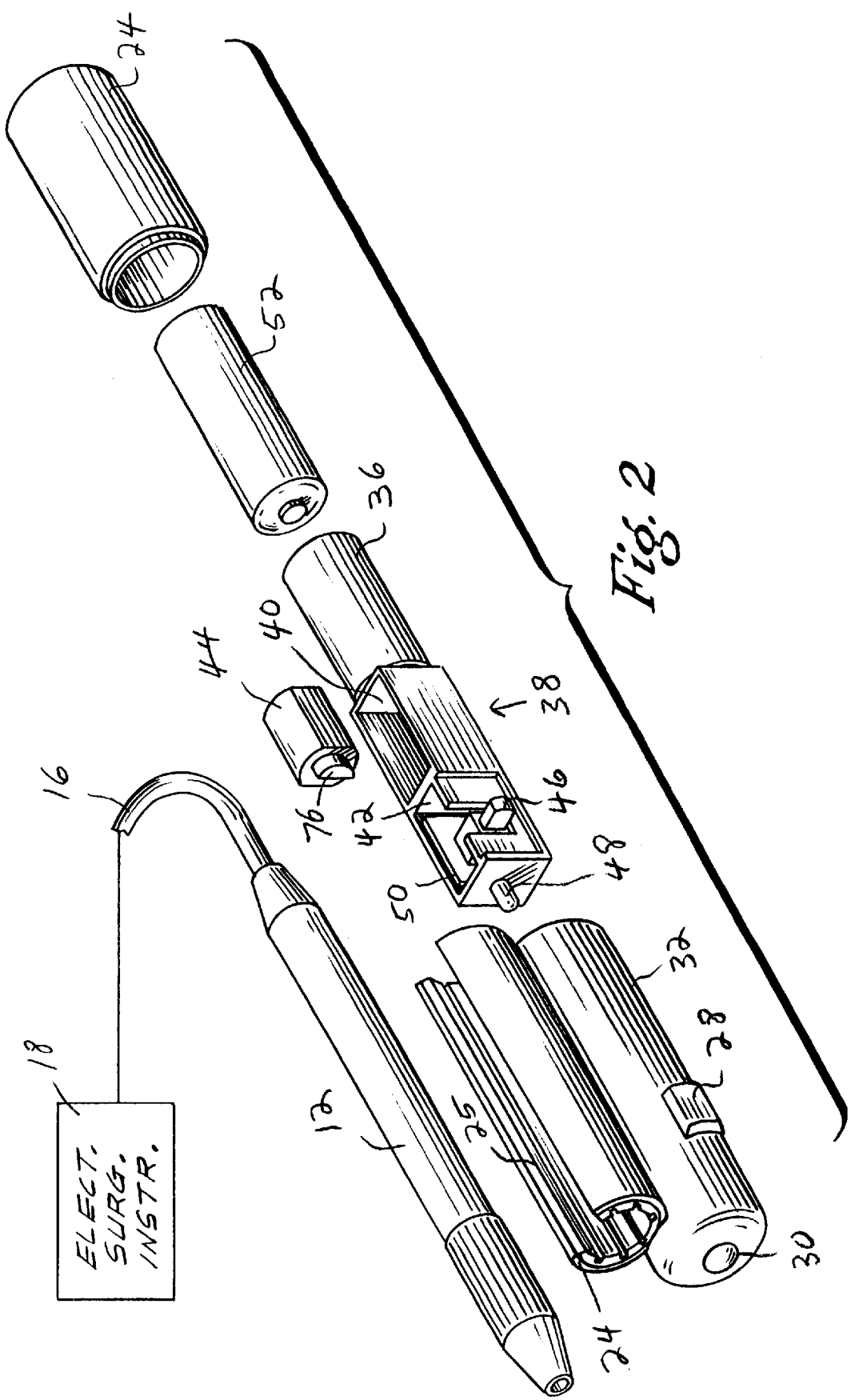
FIG. 2 is an exploded perspective view of the electrosurgical instrument of FIG. 1 showing the internal construction.

The interior construction is shown in the exploded view of FIG. 2. The assembly 26 is made up of two parts 32, 34 which can be snapped together or separated as desired. A hollow battery holder 36 is mounted to a box 38 having two compartments 40, 42. The rear compartment 40 houses a small vibrating DC motor 44. The front compartment 42 houses a pushbutton switch 46, a small light bulb 48 which projects froward of the front wall, and a small circuit board 50 with wires or connections (not shown as obvious and simple) interconnecting by way of the circuit board 50 the DC motor 44, the switch 46 and the light bulb 48, such that, when the pushbutton is depressed, the motor vibrates and the light bulb lights. The latter is positioned such that its light rays 51 (FIG. 1) can pass out through the front opening 30 to illuminate the operative site. The assembly is formed by placing a battery 52 into its holder 36 (the wires or contacts connecting the two terminals of the battery to the circuit board are not shown), mounting the motor 44 into its compartment 40, and snapping the rear part of the housing 34 onto the front part 32. The pushbutton cover 28 is positioned to cover the pushbutton switch 46. Then the handpiece 12 can be placed into its holder 24 where it is gripped by the rubber lining 25. The assembly is then ready for use.

Figure 3:
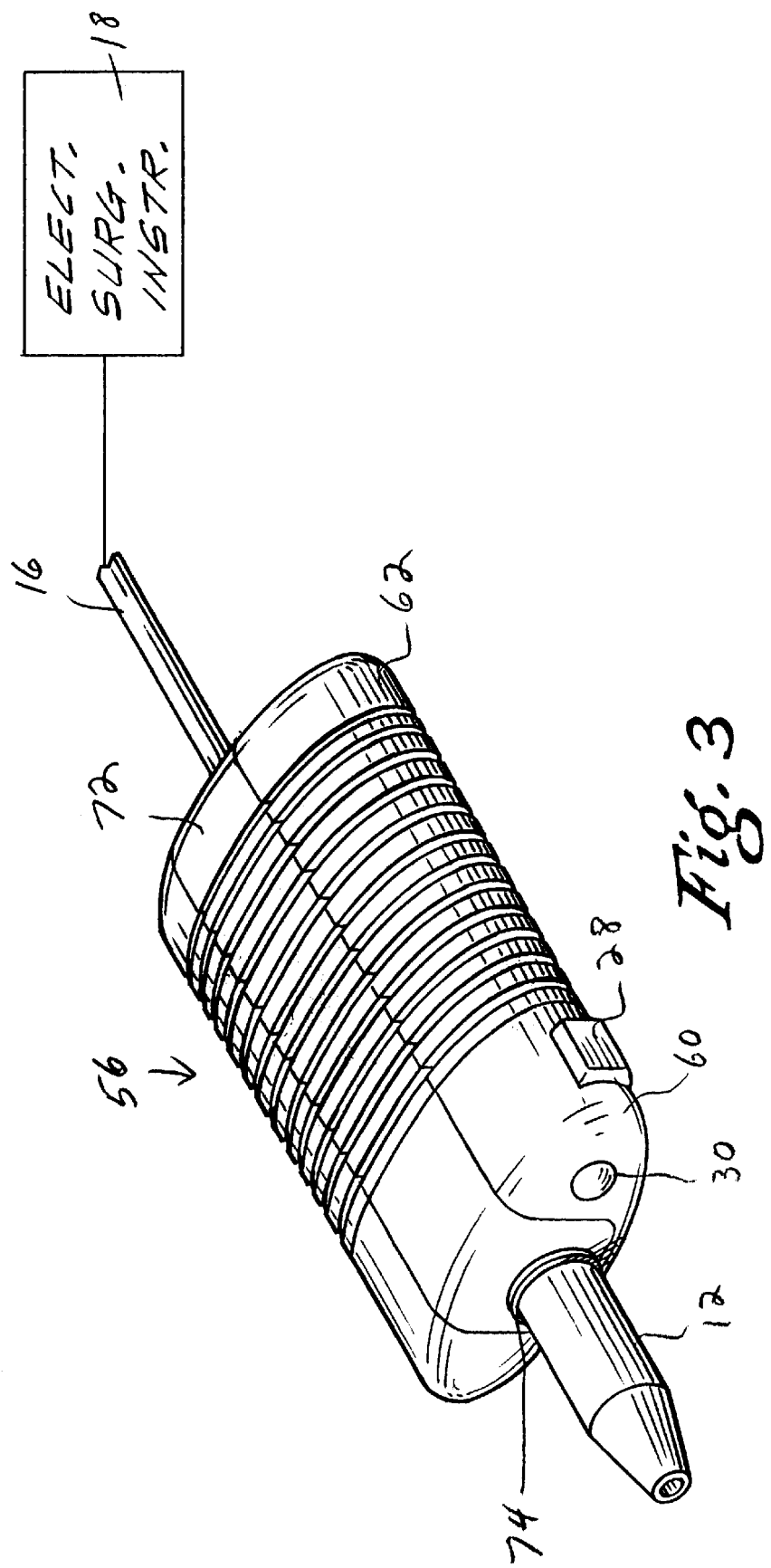
FIG. 3 is a perspective view of another form of electrosurgical instrument in accordance with the invention.
Figure 4:
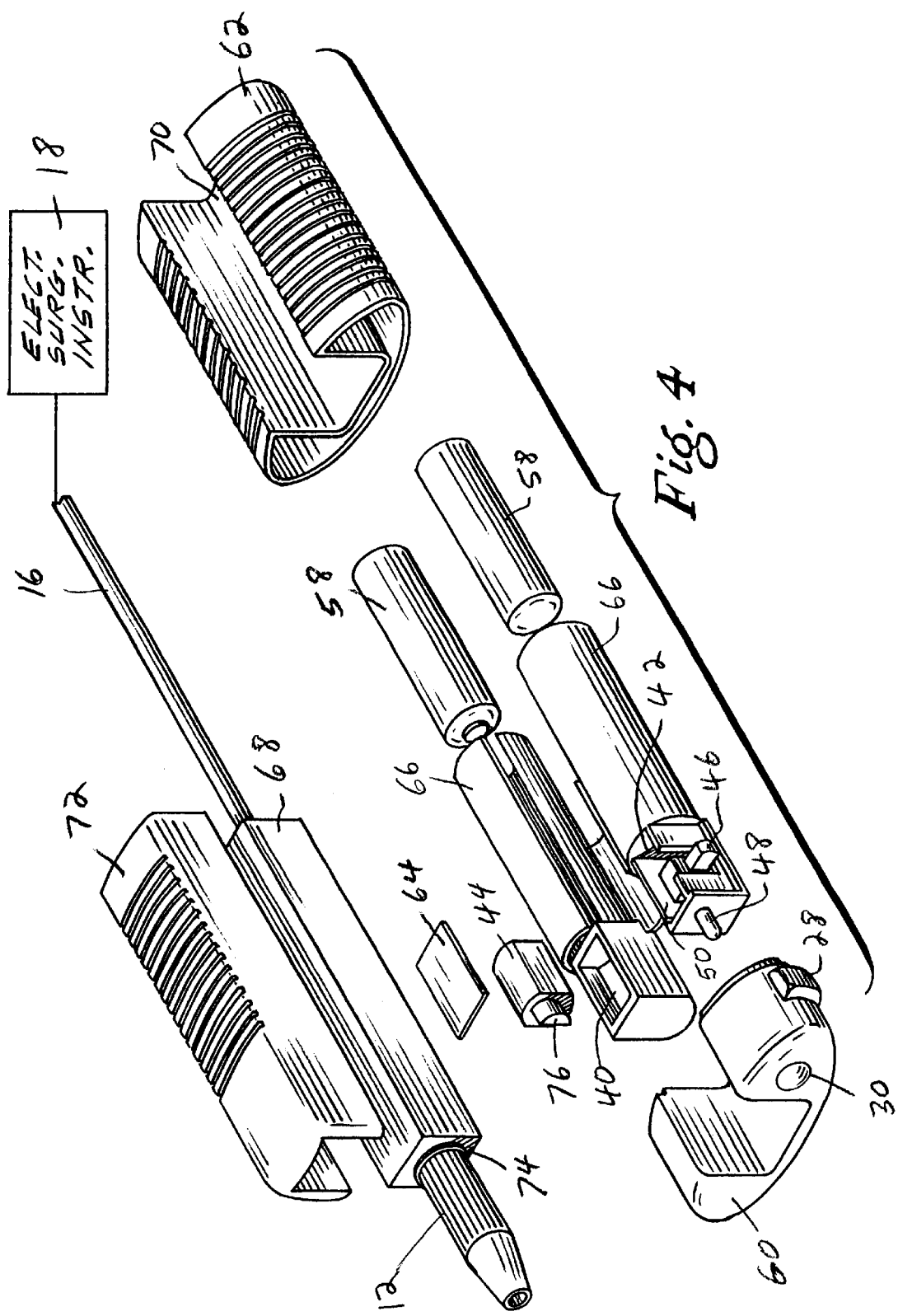
FIG. 4 is an exploded perspective view of the electrosurgical instrument of FIG. 3 showing the internal construction.

FIGS. 3 and 4 are perspective and exploded views of a variation, in which similar items are designated by the same reference numerals. The main differences are that the FIGS.

3 and 4 embodiment 56 is wider and shorter and accommodates two batteries 58. The wider shape may be preferred by certain surgeons. As before, the outer housing is split into front and rear sections 60, 62 that snap together and separate to change batteries. The front half 60 accommodates separate compartments 40, 42, the former to house the vibrating DC motor 44 and the latter to house the switch 46, the circuit board 50 and the light bulb 48. The interconnections, again, are not shown for simplicity. A cover 64 is also shown for the motor compartment. The batteries are received in separate compartments 66 which are located in the hollow spaces in the rear part 62. The standard handpiece 12 is removably gripped rectangular member 68 lined on its interior with rubber 74. A U-shaped cover 72 fits over the rectangular member 68 and in turn seats within the hollow space 70 of the generally U-shaped rear part 62. The assembly is shown in FIG. 3 and operates in the same manner as that of FIG. 1.

The pushbutton switch can also be of another kind such as a slide switch. Also the manner in which the motor and switch are mounted in the housing as well as how the handpiece is attached to the housing can also be varied without departing from the teachings of the invention. What is important in the preferred embodiments is that the vibrations are caused not by an expensive energy-hungry ceramic transducer, but by an inexpensive fractional-horsepower vibrator motor commercially available. Such motors are well known in the art and are constructed so as to be unbalanced, for example, with eccentric shafts or eccentric cams, as in the example shown at 76, and when activated by a low-voltage DC source, the eccentric rotor rotating at a speed of about 10K rpm causes the unbalanced motor to physically vibrate at an ultrasonic frequency. The vibrations of the motor are transmitted to its housing and in turn to the attached handpiece. The result is that the entire apparatus vibrates at the ultrasonic frequency indicated, and so does the electrode 20 held by the handpiece. This causes the electrode's working end also to have ultrasonic energy imparted to it producing the advantageous results described above. The vibrations do not have a high intensity, but nevertheless the working end of the electrode is subjected to ultrasonic energy to assist in the cutting or coagulation. Motors with a horsepower of about 1/8 have been used satisfactorily, but it will be understood that the invention is not so limited and motors with other horsepowers will also be effective. The light while desirable can be omitted if desired. The shape of the electrode working end will be chosen in accordance with the desires of the surgeon. Certain shapes are well known and preferred for certain procedures. The Ellman catalogs illustrate the various shapes available and the procedures for which they are best suited. The versatility of the unit is evidenced by making the handpiece removal from the assembly if the surgeon desires not to use the vibratory effect.

While the preferred embodiments illustrate a vibrating attachment for a standard handpiece, it will be understood that the parts can be permanently assembled if so desired.

Suction can also be combined with the vibrating handpiece to remove smoke, and fluid and irrigation can be added as well to enhance the effect of tissue interaction with the vibration that creates minimal contact with the tissue or maximum effect of the radio frequency that effects the water molecules by adding appropriate suction or fluid conduits to the handpiece. The addition of a fluid will in particular enhance the performance of a skin resurfacing or other surgical procedures.

While the preferred embodiments use a battery-driven dc motor, it will be understood that the battery-driven dc motor can be replaced by an ac motor or any kind of motor or another vibrating device, either mechanical or electronic, operated by batteries or alternatively by an ac source connected by a line cord to the handpiece if the effect of the other vibrating device is to impart ultrasonic energy to the electrosurgical electrode activated by RF currents. Alternatively, the electrical power needed to operate the vibrating device can be derived from the electrosurgical apparatus supplying the electrosurgical currents. Such apparatus is connected to an ac source and typically comprises a transformer from whose windings the voltages needed to operate the electrosurgical circuitry are derived, and can readily supply another voltage which can be supplied to the handpiece via the appartus cable to operate the vibrating device if desired.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical instrument providing ultrasonic energy, comprising:
   (a) a housing having a device for generating ultrasonic energy,
   (b) a handpiece for holding an electrosurgical electrode, said handpiece being mounted to the housing,
   (c) means for supplying electrosurgical currents to the handpiece and via the handpiece to the electrode,
   (d) means for activating the device for generating ultrasonic energy such that ultrasonic energy is imparted to the electrode while electrosurgical currents can be applied to the electrode, wherein, the device for generating ultrasonic energy comprises an unbalanced motor mounted in the housing.

2. An electrosurgical instrument as claimed in claim 1, wherein the housing comprises one or more batteries for activating the device for generating ultrasonic energy.

3. An electrosurgical instrument as claimed in claim 1, wherein the housing comprises means for illuminating a region adjacent to the electrosurgical electrode.

4. An electrosurgical instrument providing ultrasonic energy, comprising:
   (a) a housing having a device for generating ultrasonic energy,
   (b) a handpiece for holding an electrosurgical electrode, said handpiece being mounted to the housing,
   (c) means for supplying electrosurgical currents to the handpiece and via the handpiece to the electrode,
   (d) means for activating the device for generating ultrasonic energy such that ultrasonic energy is imparted to the electrode while electrosurgical currents can be applied to the electrode, wherein the device for generating ultrasonic energy is a DC vibrating motor.

5. An electrosurgical instrument as claimed in claim 4, wherein the housing comprises one or more batteries for activating the device for generating ultrasonic energy.

6. An electrosurgical instrument as claimed in claim 4, further comprising a handpiece holder attached to the housing, the handpiece being removably mounted in the handpiece holder.

7. In combination:
   (a) a handpiece having means at one end for connection to electrosurgical apparatus capable of supplying high frequency RF currents and having at its opposite end means for mounting the electrically-conductive shaft of an electrosurgical electrode and for supplying the high frequency currents to said electrode;

(b) means for generating ultrasonic energy such that ultrasonic energy is imparted to the electrode while electrosurgical currents can be applied to the electrode.

(c) wherein the means for generating ultrasonic energy comprises a fractional-horsepower DC unbalanced motor.

8. The combination of claim 7, wherein the unbalanced motor rotates at about 18–12K rpm.

9. The combination of claim 7, wherein the high frequency currents are at a frequency exceeding 2 MHz.

10. The combination of claim 7, wherein the high frequency currents are at a frequency of about 4 MHz.

11. A surgical procedure for a patient, comprising the steps:

(a) providing electrosurgical apparatus connected to a handpiece holding an electrosurgical electrode, (b) providing a source of ultrasonic energy that can be imparted to the electrosurgical electrode, wherein the source of ultrasonic energy comprises a fractional-horsepower unbalanced motor rotating at a speed that will impart ultrasonic vibrations to the handpiece, (c) applying the electrosurgical electrode to a surgical site of patient while activating the electrosurgical apparatus and the source of ultrasonic energy.

12. A surgical procedure for a patient as claimed in claim 11, wherein the electrosurgical apparatus supplies electrosurgical currents of about 4 MHz to the electrode.

13. A surgical procedure for a patient as claimed in claim 12, wherein the source of ultrasonic energy comprises a fractional-horsepower unbalanced motor rotating at a speed of about 10K rpm.

* * * * *